US012496206B2

(12) United States Patent
Avenant

(10) Patent No.: US 12,496,206 B2
(45) Date of Patent: Dec. 16, 2025

(54) WEARABLE DEVICE FOR INCREASED MOBILITY

(71) Applicant: Ankle Thingy LLC, Houston, TX (US)

(72) Inventor: Christopher Avenant, Houston, TX (US)

(73) Assignee: Ankle Thingy LLC, Houston, TX (US)

( * ) Notice: Subject to any disclaimer, the term of this patent is extended or adjusted under 35 U.S.C. 154(b) by 578 days.

(21) Appl. No.: 17/835,874

(22) Filed: Jun. 8, 2022

(65) Prior Publication Data

US 2022/0387203 A1 Dec. 8, 2022

Related U.S. Application Data

(60) Provisional application No. 63/208,088, filed on Jun. 8, 2021.

(51) Int. Cl.
*A61F 5/01* (2006.01)
*G06F 1/16* (2006.01)

(52) U.S. Cl.
CPC ............ *A61F 5/0111* (2013.01); *G06F 1/163* (2013.01)

(58) Field of Classification Search
CPC .... A61F 5/0111; A61F 5/0127; A61F 13/066; A61F 5/0102; A61F 5/0585; A61F 5/0116; A61F 7/10; A61F 2007/0044; A61F 2013/00187; A61G 13/123; A43B 5/1691; A43B 7/20
See application file for complete search history.

(56) References Cited

U.S. PATENT DOCUMENTS

| | | | | |
|---|---|---|---|---|
| 5,177,884 | A * | 1/1993 | Rullier ................. | A43B 5/0411 36/114 |
| 6,053,884 | A * | 4/2000 | Peters ................... | A61F 5/0127 602/5 |
| 7,032,246 | B1 * | 4/2006 | LeMire ................ | A41D 15/005 2/22 |

* cited by examiner

*Primary Examiner* — Ophelia A Hawthorne
(74) *Attorney, Agent, or Firm* — Kirby Drake

(57) ABSTRACT

A wearable device that passively and/or actively massages the muscles and tendons on the front of the ankle enabling increased mobility. The device uses adjustable half spheres that come in various sizes and materials such as wood and/or acrylic to apply pressure to the various areas of the ankle inhibiting myofascial release. A fixed elastic strap may wrap around the bottom of the foot and an adjustable strap may wrap around the back across the Achilles tendon. It allows for the same techniques to be applied passively by the user without the assistance of anyone else.

12 Claims, 5 Drawing Sheets

WEARABLE DEVICE FOR INCREASED MOBILITY

CROSS-REFERENCE TO RELATED APPLICATION

The present application is a non-provisional of, and claims priority to, U.S. Patent Application No. 63/208,088 filed Jun. 8, 2021, the disclosure of which is incorporated by reference in its entirety.

FIELD OF THE DISCLOSURE

The present disclosure generally relates wearable devices to support increased mobility, and more particularly to wearable devices that support increased mobility through active and passive myofascial release of the anterior muscles and tendons of the ankle.

BACKGROUND

Most ankle mobility practices include manual manipulation of the soft tissue of the ankle, massage, or using rubber bands to manipulate, or facilitate, improved range of motion. This requires physical exertion by both the professional (coach, personal trainer, physical therapist, orthopedic surgeon and the patient/client/athlete). Impaired dorsiflexion or plantar flexion leads to injuries and inhibits performance in daily function or physical activity.

SUMMARY

Embodiments of the present disclosure may provide a wearable device that may passively and/or actively massage the muscles and tendons on the front of the ankle enabling increased mobility. The device according to embodiments of the present disclosure may use adjustable half spheres that come in various sizes and materials such as wood and/or acrylic to apply pressure to the various areas of the ankle inhibiting myofascial release. A fixed elastic strap may wrap around the bottom of the foot and an adjustable strap may wrap around the back across the Achilles tendon. Use of the wearable device according to embodiments of the present disclosure may allow for the same techniques to be applied passively by the user without the assistance of anyone else.

Embodiments of the present disclosure may provide a wearable device for improved mobility comprising at least one fixed elastic strap that may wrap around a bottom/inferior part of a foot; an adjustable strap that may wrap around a back/posterior part of the foot across the Achilles tendon; and a plurality of half spheres with hook and loop attachments capable of being placed, removed, and adjusted to apply pressure to one or parts of an ankle, wherein the wearable device may provide passive myofascial release leading to improved dorsi and plantar flexion. The plurality of half spheres may be adjustable and may be provided in a plurality of sizes to personalize a fit of the wearable device. The wearable device may be used by a user without assistance from another. The wearable device may be formed of one or more materials selected from the group comprising: fabric, rubber, hook and loop, and elastic. The at least one fixed strap and the adjustable strap may be stitched together to form the wearable device that may conform to an ankle.

Further embodiments of the present disclosure may provide a wearable device for improved mobility of an ankle comprising a calf body defining a first frontal side and a second frontal side; a frontal opening spacing the first frontal side and the second frontal side; and opposed first and second ankle struts that may pivotally attach to the calf body. The wearable device may further include an underfoot elastic portion that may connect to the opposed first and second ankle struts. The wearable device may also include a plurality of spheres with fastening mechanisms capable of being placed, removed, and adjusted to apply pressure to one or parts of the ankle. The fastening mechanisms may be hook and loop fasteners.

Other embodiments of the present disclosure may provide a method of using a wearable device for improved mobility of an ankle comprising placing the wearable device on the ankle of a user, the wearable device comprising at least one fixed elastic strap that may wrap around a bottom/inferior part of a foot; an adjustable strap that may wrap around a back/posterior part of the foot across the Achilles tendon; and a plurality of half spheres with hook and loop attachments capable of being placed, removed, and adjusted; and adjusting the plurality of half spheres to apply pressure to one or more parts of the ankle. The wearable device may be placed in contact with the user's ankle or may be placed over an article of clothing of the user.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1A:
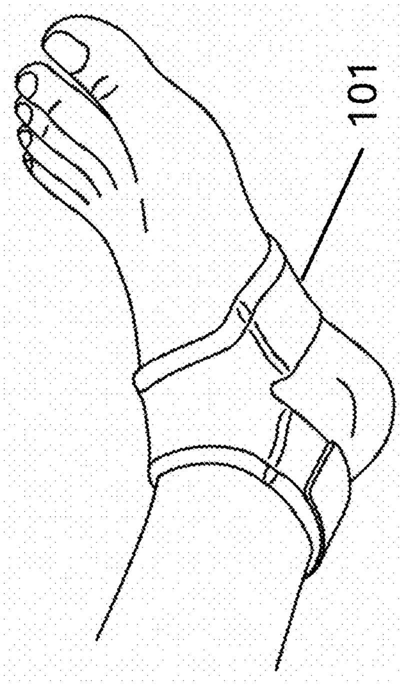
FIGS. 1A-1B depict different forms of ankle braces according to embodiments of the present disclosure.

Embodiments of the present disclosure may provide a wearable device that may allow the user to improve the mobility of his/her ankle(s) without the assistance of anyone else, creating autonomy in one's personal mobility practices, and reducing the likelihood of further injury. A wearable device according to embodiments of the present disclosure may allow personalization of mobility practices, improved range of motion (ROM) and functional movement, and accessibility through providing a portable, easy-to-use product. The wearable device may massage a user's ankle by using the natural movement in the user's ankles to add pressure to the necessary areas to relieve ankle pain, ankle stiffness, and increase ankle mobility.

A wearable device according to embodiments of the present disclosure may provide a strap worn around the user's ankle. Wooden balls, or spheres, may dig into the user's anterior muscles and tendons similar to what a physical therapist or chiropractor would do after an ankle sprain or impingement. This may result in more ankle mobility and provides relief for anyone suffering from ankle pain or stiffness. Increased ankle flexibility also may help alleviate knee pain, hip pain, and even back pain which often originates from poor ankle mobility.

A wearable device according to embodiments of the present disclosure may include at least one fixed elastic strap that may wrap around the bottom/inferior part of the foot and an adjustable strap that may wrap around the back/posterior part, across the Achilles tendon. The device according to embodiments of the present disclosure may use adjustable or fixed half spheres that come in various sizes (small, medium and large) with hook and loop attachments. Because these spheres can be placed, removed, and adjusted to apply pressure to the preferred or concerning areas of the ankle, the user may experience a personalized treatment and outcome as to increased or improved mobility.

A wearable device according to embodiments of the present disclosure may provide passive myofascial release to the inferior and superior extensor retinaculum, extensor digitorum longus tendons and brevis muscles, leading to improved dorsi and plantar flexion. Use of the wearable device does not require a trained professional to assist, thereby allowing a more efficient and effective way to release tight ankles that may have impaired range of motion. Due to personal use when needed, and without the need of anyone else, users may be more likely to have effective long-term results.

As described in detail herein, a wearable device according to an embodiment of the present disclosure may include a strap that that may wrap around the bottom/inferior part of the foot and behind/posterior part of the ankle. The part behind the ankle may be adjustable using a hook and loop fastener or another similar fastening method. Using a hook and loop strap on the inside of the wearable device, a user or manufacturer may place adjustable or fixed objects, such as half spheres, that may apply pressure to desired areas. A wearable device according to embodiments of the present disclosure may be adjusted using a hook and loop fastener or other similar fastening method to apply different levels of pressure or to adjust where pressure may be applied. It should be appreciated that the device may be formed of various materials including, but not limited to, fabric, rubber, hook and loop, and elastic in embodiments of the present disclosure. The components forming the device may be stitched together to provide a device that may conform to the ankle.

Figure 1B:
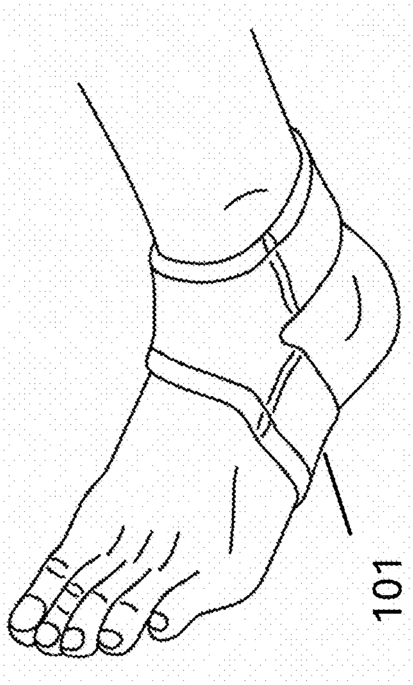
Figure 8A:
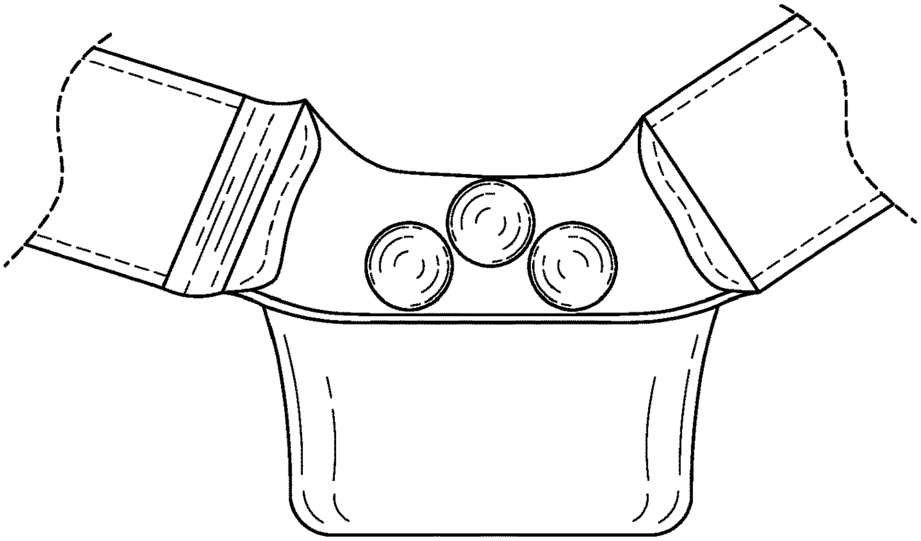
FIGS. 8A-8C depict different formations of a wearable device according to embodiments of the present disclosure.
Figure 8B:
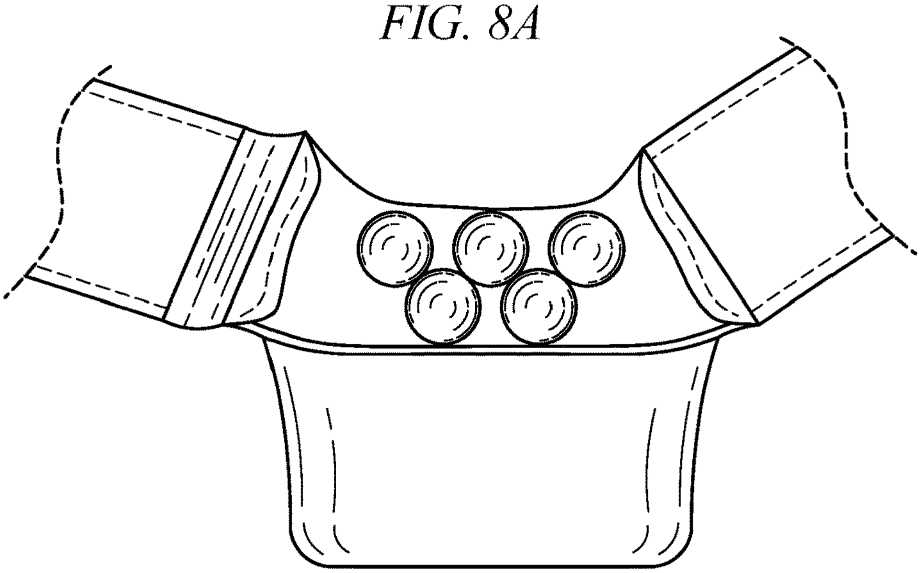
Figure 8C:
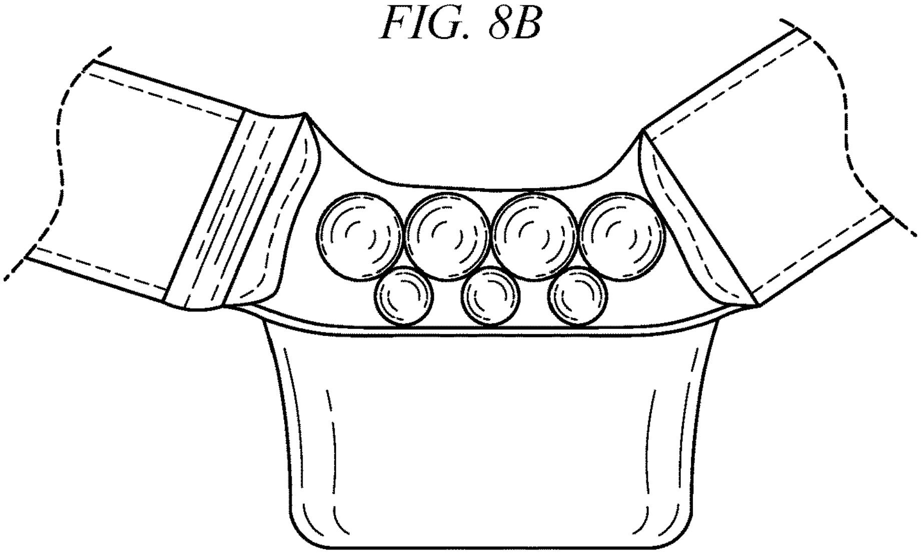

FIGS. 1A-1B depict different forms of ankle braces according to embodiments of the present disclosure. More specifically, FIG. 1A depicts an ankle brace viewed from the right side of a foot, and FIG. 1B depicts an ankle brace viewed from the left side of a foot. It should be appreciated that ankle braces may be full wear and may be lateral and/or medial in embodiments of the present disclosure. FIGS. 8A-8C depict different formations of a wearable device according to embodiments of the present disclosure.

Figure 2:
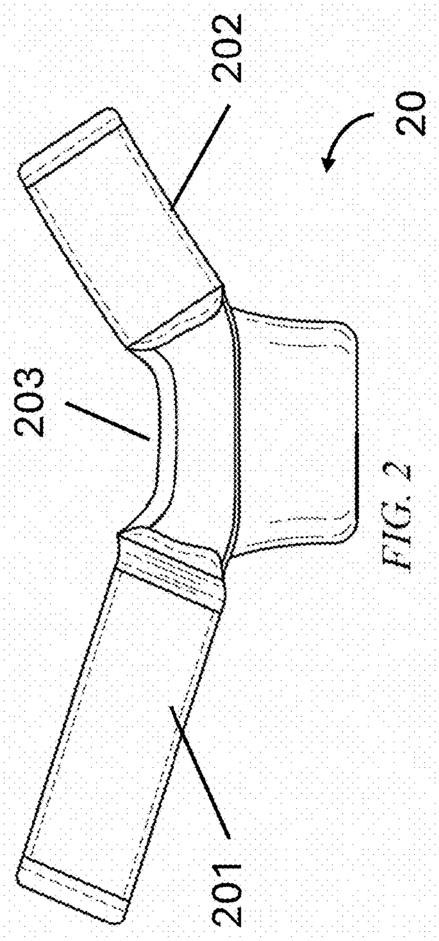
FIG. 2 depicts first and second frontal sides of an ankle brace according to an embodiment of the present disclosure.
Figure 3:
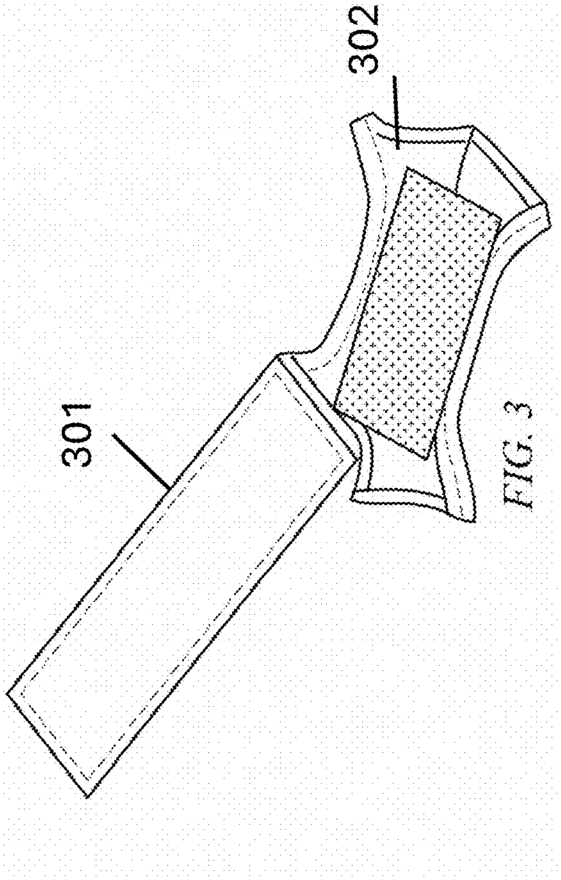
FIG. 3 depicts opposed first and second ankle struts that may pivotally attach to the calf body of an ankle brace according to an embodiment of the present disclosure.
Figure 4:
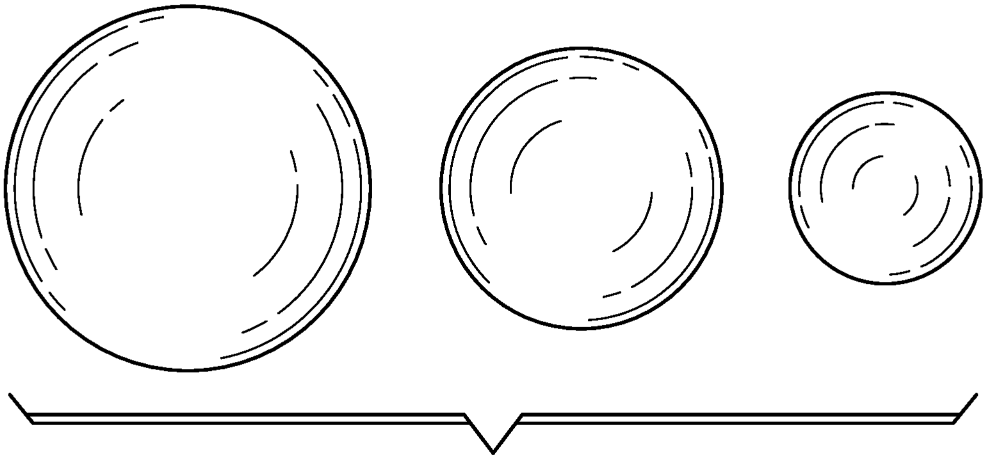
FIG. 4 depicts different size spheres according to an embodiment of the present disclosure.
Figure 5:
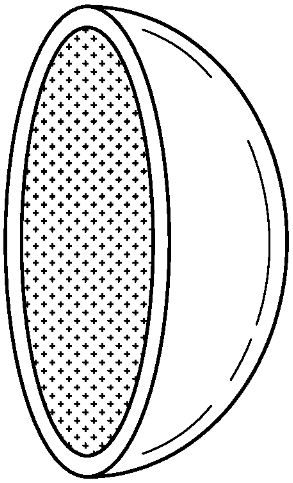
FIG. 5 depicts a hook and loop on half sphere according to an embodiment of the present disclosure.

An ankle brace according to embodiments of the present disclosure may provide calf body 20 defining first and second frontal sides 201, 202 as depicted in FIG. 2. Those frontal sides 201, 202 may be spaced by frontal opening 203 in an embodiment of the present disclosure. FIG. 3 depicts opposed first and second ankle struts 301, 302 that may pivotally attach to calf body 20 according to an embodiment of the present disclosure. There may be underfoot elastic portion 101 (FIGS. 1A, 1B) that may connect to the ankle struts 301, 302. Different size spheres as depicted in FIG. 4 may be provided to ensure a personalized experience. A user may use the hook and loop on half sphere, as depicted in FIG. 5, to apply and reapply or adjust according to his/her needs.

Figure 6:
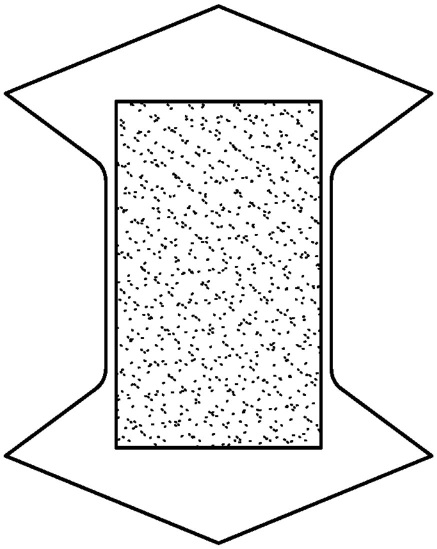
FIG. 6 depicts a main piece forming a wearable device according to an embodiment of the present disclosure.
Figure 7:
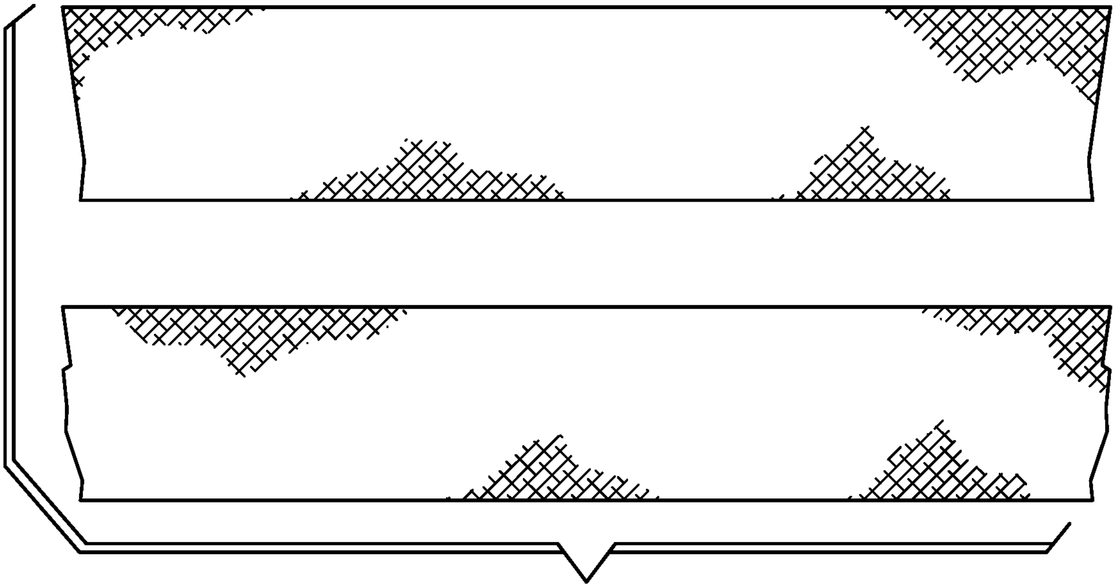
FIG. 7 depicts a binding for a wearable device according to an embodiment of the present disclosure.

FIG. 6 depicts a main piece forming a wearable device according to an embodiment of the present disclosure. While only one main piece may be depicted in FIG. 6, it should be appreciated that two main pieces may be utilized to produce a wearable device according to an embodiment of the present disclosure. These main pieces may be formed of a material such as neoprene or other rubber materials in embodiments of the present disclosure. A binding, such as the bindings depicted in FIG. 7, may be used to bind the main pieces (FIG. 6) together. This binding may be formed of a thin stretch material, such as lycra, in embodiments of the present disclosure. An underfoot elastic portion may go onto the bottom of the user's foot. Soft hook and loop pieces may be provided along with long and short ankle elastic piece and a hook and loop ankle piece.

The soft hook and loop pieces may be sewed onto a main piece, and then the main pieces may be sewn together. Slits which may be 1 cm in size may be cut at the ends. A binding may be affixed or attached to bind the main pieces together. A long ankle elastic piece may be sewed on, followed by a short ankle elastic piece, and then the elastic seams may be sewed flat. Foot elastics may then be attached, and the foot elastic seams may be sewed flat. Finally, the elastic ends may be folded over and sewed. It should be appreciated that the device according to embodiments of the present disclosure can be made using a sewing machine, any variety of fabrics and elastics, and any objects that can apply pressure to the ankle when applied. The objects can be adjustable or fixed, for example, using a hook and loop fastener, or adhesive, or directly glued to the device. The objects may be placed between the device and ankle.

The wearable device formed as described herein may provide a comfortable, confirmative device that can be worn by the user to apply pressure using adjustable objects passively and actively to desired targeted areas of the ankle. The materials used to form the wearable device according to embodiments of the present disclosure may secure pressure through the placed objects (i.e., half sphere balls) on the ankle in areas desired by the user to loosen the fascia, muscles, and/or tendons in that area(s) to increase ankle mobility. The type of fabrics, or adjustable methods, the objects used to apply pressure, or flexibility in the placement of the objects placed on the device may vary according to embodiments of the present disclosure.

In use, a user may wear the ankle brace (wearable device) over the ankle, either under or over other garments, such as socks. The user may then make adjustments to correct for tightness, for example, or object placement to meet the user's desired comfort and/or target areas.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A wearable device for improved mobility comprising:

at least one fixed elastic strap configured to wrap around a bottom/inferior part of a foot;

an adjustable strap configured to wrap around a back/posterior part of the foot across the Achilles tendon; and a plurality of half spheres with hook and loop attachments capable of being placed, removed, and adjusted to apply pressure to one or parts of an ankle, wherein the wearable device provides passive myofascial release leading to improved dorsi and plantar flexion.

2. The wearable device of claim 1, wherein the plurality of half spheres are adjustable.

3. The wearable device of claim 1, wherein the plurality of half spheres are provided in a plurality of sizes to personalize a fit of the wearable device.

4. The wearable device of claim 1, wherein the wearable device is passively used by a user.

5. The wearable device of claim 1, wherein the wearable device is formed of one or more materials selected from the group consisting of:

fabric, rubber, hook and loop, and elastic.

6. The wearable device of claim 1, wherein the at least one fixed elastic strap and the adjustable strap are stitched together to form the wearable device configured to conform to an ankle.

7. A wearable device for improved mobility of an ankle comprising:

a calf body defining a first frontal side and a second frontal side;

a frontal opening spacing the first frontal side and the second frontal side;

a plurality of spheres with fastening mechanisms capable of being placed, removed, and adjusted to apply pressure to one or more parts of the ankle; and opposed first and second ankle struts that pivotally attach to the calf body.

8. The wearable device of claim 7 further comprising:

an underfoot elastic portion that connects to the opposed first and second ankle struts.

9. The wearable device of claim 7, wherein the fastening mechanisms are hook and loop fasteners.

10. A method of using a wearable device for improved mobility of an ankle comprising:

placing the wearable device on the ankle of a user, the wearable device comprising at least one fixed elastic strap that wraps around a bottom/inferior part of a foot; an adjustable strap that wraps around a back/posterior part of the foot across the Achilles tendon; and a plurality of half spheres with hook and loop attachments capable of being placed, removed, and adjusted;

and adjusting the plurality of half spheres to apply pressure to one or more parts of the ankle.

11. The method of claim 10, wherein the wearable device is placed in contact with the user's ankle.

12. The method of claim 10, wherein the wearable device is placed over an article of clothing of the user.

* * * * *